(12) United States Patent
Tegen et al.

(10) Patent No.: US 11,724,977 B2
(45) Date of Patent: *Aug. 15, 2023

(54) PROCESSES FOR SOLVENT EXTRACTION OF CANNABINOIDS, TERPENES AND FLAVONOIDS FROM BIOMASS

(71) Applicant: SOCATI TECHNOLOGIES—OREGON, LLC, Austin, TX (US)

(72) Inventors: Mark G. Tegen, Seattle, WA (US); Joon Cho, Tumwater, WA (US); William Rusty Sutterlin, Tuscaloosa, AL (US)

(73) Assignee: SOCATI TECHNOLOGIES—OREGON, LLC, Austin, TX (US)

( * ) Notice: Subject to any disclaimer, the term of this patent is extended or adjusted under 35 U.S.C. 154(b) by 90 days.

This patent is subject to a terminal disclaimer.

(21) Appl. No.: 17/203,636

(22) Filed: Mar. 16, 2021

(65) Prior Publication Data

US 2021/0238117 A1    Aug. 5, 2021

Related U.S. Application Data

(63) Continuation of application No. 16/538,487, filed on Aug. 12, 2019, now Pat. No. 10,961,174, which is a continuation of application No. 16/447,853, filed on Jun. 20, 2019, now Pat. No. 10,414,709, which is a continuation-in-part of application No. 16/259,616, filed on Jan. 28, 2019, now Pat. No. 10,413,845.

(60) Provisional application No. 62/781,958, filed on Dec. 19, 2018, provisional application No. 62/779,862, filed on Dec. 14, 2018.

(51) Int. Cl.
*C07C 37/68* (2006.01)
*B01D 11/02* (2006.01)
*C07C 37/00* (2006.01)

(52) U.S. Cl.
CPC ........ *C07C 37/685* (2013.01); *B01D 11/0288* (2013.01); *C07C 37/004* (2013.01); *C07C 2601/14* (2017.05); *C07C 2601/16* (2017.05)

(58) Field of Classification Search
None
See application file for complete search history.

(56) References Cited

U.S. PATENT DOCUMENTS 9,340,475 B2 * 5/2016 Mona, III ............... C07C 37/74

* cited by examiner

*Primary Examiner* — Michael V Meller
(74) *Attorney, Agent, or Firm* — Flener IP & Business Law; Zareefa B. Flener (57) ABSTRACT

In alternative embodiments, provided are industrial processes and methods for extracting or removing cannabinoids, flavonoids and terpenes from plant materials such as trichomes. In alternative embodiments, the cannabinoids, flavonoids and terpenes are extracted or removed from the plant materials using a non-polar, organic solvent, or a mixture of non-polar, organic solvent and polar, organic solvent.

24 Claims, 1 Drawing Sheet

PROCESSES FOR SOLVENT EXTRACTION OF CANNABINOIDS, TERPENES AND FLAVONOIDS FROM BIOMASS

RELATED APPLICATIONS

This U.S. Utility patent application is a continuation-in-part (CIP) of and claims the benefit of priority under 35 U.S.C. § 120 of U.S. patent application Ser. No. 16/447,853 filed Jun. 20, 2019 (now pending), which is a CIP of and claims benefit of priority to U.S. Ser. No. 16/259,616, filed Jan. 28, 2019 (now pending), which claims benefit of priority to U.S. Provisional Application Ser. No. 62/779,862, filed Dec. 14, 2018, and U.S. Ser. No. 62/781,958, filed Dec. 19, 2018. The aforementioned applications are expressly incorporated herein by reference in their entirety and for all purposes.

FIELD OF THE INVENTION

This invention generally relates to chemical engineering and organic chemistry. In alternative embodiments, provided are industrial processes and methods for extracting or removing cannabinoids, flavonoids and terpenes from plant materials such as trichomes. In alternative embodiments, the cannabinoids, flavonoids and terpenes are extracted or removed from the plant materials using: a non-polar, organic solvent; a polar, organic solvent; or, a mixture of non-polar, organic solvent and polar, organic solvent.

BACKGROUND

The production of trichomes can be observed in many species of plants throughout nature, taking on various physical forms as well as serving many different purposes. For example, trichomes found on some carnivorous plants aid in helping to catch prey. In *cannabis*, trichomes function as a defense mechanism. When female *cannabis* plants begin to produce flowers in the wild, they often become vulnerable to various insects and animals as well as non-living environmental variables such as potentially harmful UV rays. Trichomes serve as a deterrent for animals because their bitter taste and strong aromas render *cannabis* flowers unpalatable. At the same time, they also serve a dual function in protecting their plants from damaging winds and even some varieties of fungal growth. Bulbous trichomes are the smallest of the bunch, and they appear on the surface of the entire plant. Bulbous trichomes are as small as 10-15 micrometers, which is tiny enough to only be comprised of a handful of cells. Capitate sessile trichomes are slightly larger and contain both a head and a stalk. Capitate-stalked trichomes range from anywhere between 50-100 micrometers wide, meaning they're much larger and can actually be seen by the naked eye. Their structure consists of a stalk comprised of epidermal and hypodermic cells that build up to a basal cell which attaches to a large gland head. This gland head, held together by a waxy cuticle layer, serves as the epicenter for cannabinoid and terpenoid synthesis.

The importance of the process of extraction has increased with the growing global awareness of the medicinal, wellness and nutritional benefits of *Cannabis* plant extracts. In the example of hemp species of *Cannabis* it has been discovered that compounds present on the plant provide medicinal benefit for such conditions as inflammation, pain, nausea and epilepsy. There are some 60 bio-active compounds within the *Cannabis* plant. Some of these compounds are predicted to be valuable natural-source drugs which may not be associated with the side effects which plague commercial synthetic drugs.

Various methods of solvent extraction have been developed to separate the cannabinoids and terpenes from the non-cannabinoid and terpene biomaterial. Concentration of the cannabinoids and terpenes by solvent extraction is widely practiced and allows for the development of a wide variety of consumer products such as cannabinoid containing baked goods, gummies, sprays, drinks and other forms of cannabinoid products.

Industry has evolved three primary methods of solvent extraction including but not limited to super critical carbon dioxide, cold ethanol extraction and compressed butane extraction. Typical industrial practice is to first dry the fresh harvested whole plant material to about 5% to 10% moisture from a starting moisture greater than 50%. Then the biomass is processed, usually by hand or a semi-automated process where each plant is individually fed into a machine by hand, to separate the plant stem and fan leaves from the flower and cannabinoid rich leaves. The flower and leaf material is then typically subjected to one of the 3 common extraction methods to obtain the cannabinoids and remaining terpenes from the dried plant.

For example, in Method for Continuous Extraction and Separation of Useful Compounds from Plant or Animal Material Patent Literature U.S. Pat. No. 6,403,126, Webster et al teaches a method of extracting cannabinoids, cannflavins or essential oils in which the solvent may be a petroleum-derived hydrocarbon (for example: toluene or trimethylpentane); a low molecular weight alcohol (for example ethanol); a low molecular weight chlorinated hydrocarbon (for example, chloroform); dichloromethane; or, supercritical fluid such as $CO_2$; and various products from hemp lacking $A^9$-THC obtained by passing the extract over a chromatographic column. U.S. Pat. No. 9,782,691, Chess et al teaches a process in which super- or sub-critical $CO_2$ is, alone or with a lower vapor pressure gas or gases, collected and re-used in a closed-loop extraction process. U.S. Pat. No. 9,399,180, Ellis et al teaches a vertical extraction process in which liquid gas is applied at the top, a vacuum draws down the extractant, and the gas is removed by cooling and recycled. U.S. Pat. No. 8,048,304, Walbel et al teaches a process for increased efficiency in the recovery and recycle of gases used in an extraction process. U.S. Pat. No. 9,358,259, Hospodor et al teaches a process of extracting cannabinoids in which the solvent is passed through the material many times in a cycle, the extractant remaining behind in a collector tank from which the solvent is removed and recycled. U.S. Pat. Nos. 9,669,328, 9,789,147, and 9,844,740, Jones, teach a process of extraction in which extraction takes place using liquid gases after which the product is used as is. The methods described lack the ability to extract cannabinoids and terpenes from the surface trichomes of whole wet plant material.

Hemp-derived cannabinoid use is rapidly expanding and more effort must be made to improve the extraction efficiency and overall extraction process economics. The current method of hand harvesting the hemp followed by drying and physical processing of the plant to remove stem and fan leaves is very costly, labor intensive and impractical when considering hand harvesting and drying thousands of acres and millions of pounds of biomass. Current extraction processes and methodology must be adapted for efficiency to modern outdoor farming and crop harvest methods. The ability to harvest the hemp biomass mechanically and process the plant in its intact and wet form will dramatically reduce the costs for growers, processors and consumers.

Clearly a method of extracting cannabinoids and terpenes from whole plant wet biomass is needed.

SUMMARY

In alternative embodiments, provided are industrial processes or methods for extracting or isolating a cannabinoid, a terpene or a flavonoid (or bioflavonoid), from a trichome or a trichome fraction of pubescent plant, algae or lichen, the method comprising:

(a) washing, contacting or exposing the trichome or trichome fraction, or the pubescent plant, algae or lichen, with: at least one non-polar, organic solvent; at least one polar, organic solvent; or, a mix of at least one non-polar, organic solvent with (and) at least one polar, organic solvent, and collecting or separating the solvent from the trichome or trichome fraction, or the pubescent plant, algae or lichen; or (b) (i) providing a pubescent plant or plant part, an algae or an algae part, or a lichen or lichen part comprising a trichome or a trichome fraction, (ii) providing: at least one non-polar, organic solvent; at least one polar, organic solvent; or, a mix of at least one non-polar, organic solvent with (and) at least one polar, organic solvent, (ii) washing, contacting or exposing the trichome or trichome fraction, or the pubescent plant, algae or lichen, with the at least one solvent or solvent mix, wherein optionally the washing, contacting or exposing is done in a reaction vessel and (iii) collecting or substantially removing the at least one solvent or solvent mix, thereby extracting or isolating (or substantially isolating) the cannabinoid, terpene or flavonoid (or bioflavonoid) from the trichome or trichome fraction of the pubescent plant, algae or lichen.

In alternative embodiments, of industrial processes or methods as provided herein:

the pubescent plant or plant part is a hemp or a marijuana plant or a plant of the family Cannabaceae;

the pubescent plant or plant part, the algae or algae part, or the lichen or lichen part, other than harvesting or collecting, is unprocessed or has not been physically processed, or has not been exposed to: a solvent or aqueous solution; a heating or drying process; a dehydration process; a crushing process; and/or, a chopping, macerating or mincing process, since (after) its harvest;

the pubescent plant or plant part, the algae or algae part, or the lichen or lichen part, other than harvesting or collecting, is subjected to: a heating or drying process; a dehydration process; a crushing process; and/or, a chopping, macerating or mincing process, since (after) its harvest;

the plant of the family Cannabaceae is a plant of the genus *Cannabis*, *Humulus* or *Celtis*, and optionally the plant of the genus *Cannabis* is a *Cannabis sativa*, *Cannabis indica* or a *Cannabis ruderalis*;

the trichome is a glandular trichome;

the trichome or trichome fraction is isolated, or is substantially isolated, from the pubescent plant, algae or lichen before the washing, contacting or exposing of the trichome or trichome fraction with the at least one solvent (e.g., polar, organic solvent; non-polar, organic solvent, or mixture thereof); and/or the trichome or trichome fraction is not isolated from the pubescent plant, algae or lichen before the washing, contacting or exposing of the trichome or trichome fraction with the at least one solvent (e.g., polar, organic solvent; non-polar, organic solvent, or mixture thereof).

In alternative embodiments, industrial processes or methods as provided herein comprise continuously extracting and separating the cannabinoid, terpene and/or flavonoid compounds from the trichome or trichome fraction, or from the pubescent plant, algae or lichen, by a method comprising:

(a) feeding the trichome or trichome fraction, or the pubescent plant, algae or lichen, into a vessel;

(b) feeding the liquid non-polar, organic solvent; polar, organic solvent; or mixture thereof into the vessel to: saturate (or substantially saturate) the trichome or trichome fraction, or the pubescent plant, algae or lichen, in the vessel with the liquid non-polar, organic solvent polar, organic solvent; or mixture thereof; or, to create a mixture of (i) liquid non-polar, organic solvent polar, organic solvent; or mixture thereof, and (ii) trichome or trichome fraction, or pubescent plant, algae or lichen, thereby dissolving the cannabinoids, terpenes and or flavonoids in (or into) the trichome or trichome fraction, or the pubescent plant, algae or lichen, into the liquid non-polar, organic solvent; polar, organic solvent; or mixture thereof, wherein optionally the vessel is heated before and/or during the feeding and/or saturating process, and optionally the vessel is heated to or kept warm or hot to between about 37° C. and 100° C., and optionally the vessel is cooled and/or kept cool before and/or during the feeding and/or saturating process, and optionally the vessel is cooled (or kept cool) to between about −20° C. and 37° C., or is cooled (or kept cool) to between about −18° C. and 22° C., or is cooled (or kept cool) to between about −10° C. and 0° C., and optionally the mixture is agitated during all or part of the saturating process, and optionally the liquid non-polar, organic solvent; polar, organic solvent; or mixture thereof, is removed, or substantially removed, from the vessel, and optionally only the liquid non-polar, organic solvent; polar, organic solvent; or mixture thereof, is removed, or substantially removed, from the vessel, or substantially most of the trichome or trichome fraction, or the pubescent plant, algae or lichen, remains in the vessel after removal of the liquid non-polar, organic solvent; polar, organic solvent; or mixture thereof.

In alternative embodiments, in the industrial processes or methods as provided herein the at least one non-polar, organic solvent comprises: an aliphatic hydrocarbon, a 1,4 dioxane, a chloroform, a dichloromethane, a diethyl ether, a terpene or a terpenoid, a hemiterpene, a monoterpene, a diterpene, a limonene, a humulene, a pinene, a myrcene, a limonene, a linanool, a caryophylene, acetone, benzene or a substituted benzene, toluene, a xylene, ethyl acetate, propyl acetate, butyl acetate, tetrahydrofuran, tetrahydropyran, or any mixture thereof.

In alternative embodiments, in the industrial processes or methods as provided herein the aliphatic hydrocarbon comprises a terpene, a pentane, a cyclopentane, a hexane, a cyclohexane, a heptane, diethyl ether, dipropyl ether, dibutyl ether or any mixture thereof.

In alternative embodiments, in the methods as provided herein the at least one non-polar, organic solvent further comprises a polar, organic solvent, to make a mixture of the polar, organic solvent and non-polar, organic solvent. In alternative embodiments, methods as provided herein use only at least one polar, organic solvent (as a solvent).

In alternative embodiments, the at least one polar, organic solvent can comprise at least one organic alcohol, and optionally the at least one organic alcohol comprises methanol, ethanol, propanol, isopropanol, butanol, pentanol, hexanol, heptanol or octanol or a mixture thereof. In alternative embodiments, the mixture of the polar, organic solvent and non-polar, organic solvent can have more polar, organic solvent than non-polar, organic solvent, or the mixture of the polar, organic solvent and non-polar, organic solvent has about 1% to 100% more polar, organic solvent than non-polar, organic solvent.

In alternative embodiments, the mixture of the polar, organic solvent and non-polar, organic solvent has more non-polar, organic solvent than polar, organic solvent.

In alternative embodiments, the washing, contacting or exposing the trichome or trichome fraction, or the pubescent plant, algae or lichen, with the at least one non-polar or organic solvent lasts for a period of between about 1 minute to about 48 hours, or for a period of time of between about 1 minute to 60 minutes, between about 1 minute to 120 minutes, or between about 1 minute to 480 minutes. In alternative embodiments, the washing, contacting or exposing the trichome or trichome fraction, or the pubescent plant, algae or lichen, with the at least one non-polar or organic solvent comprises immersion, spraying, washing, counter current liquid solid contacting or any combination thereof. In alternative embodiments, the trichome or trichome fraction, or the pubescent plant, algae or lichen, after the washing, contacting or exposing to the at least one non-polar, organic solvent, is processed for harvesting or extracting residual solvent removal, and optionally techniques or methods for harvesting or extracting residual solvent removal comprise using a screw press (optionally a dewatering screw press) or a sludge press, spray drying, air stripping, gas stripping, vacuum stripping, heating, evaporation, washing or any combination thereof.

In alternative embodiments, the industrial processes or methods as provided herein further comprise removing residual solvent (e.g., at least one non-polar, organic solvent; at least one polar, organic solvent, or mixture thereof), wherein optionally techniques or methods for removing the residual one non-polar or organic solvent comprise using a screw press (optionally a dewatering screw press) or a sludge press, spray drying, air stripping, gas stripping, vacuum stripping, heating, evaporation, washing or any combination thereof.

In alternative embodiments of the industrial processes or methods as provided herein, the trichome or trichome fraction, or the pubescent plant, algae or lichen, is fed through a conveyor into an extraction unit and optionally is sprayed (optionally continuously sprayed) with the at least one non-polar or organic solvent.

In alternative embodiments, provided are industrial processes or methods for extracting a cannabinoid or a terpene from a hemp or a *cannabis* plant or plant part, comprising: treating or exposing the hemp or *cannabis* to a solvent comprising a terpene to produce an extraction solvent comprising an extracted hemp or *cannabis* comprising the cannabinoid or the terpene from the hemp or the *cannabis* plant or plant part.

In alternative embodiments of the industrial processes or methods as provided herein:
- the *cannabis* plant or plant part is or is derived from a marijuana plant or a plant of the family Cannabaceae;
- the terpene solvent comprises: humulene, pinene (optionally α-pinene), myrcene, limonene, linanool, caryophylene, carene, camphene, dipentene, terpinolene or turpentine, or any combination thereof; or, the terpene solvent comprises: a hemiterpene (optionally a prenol or an isovaleric acid); a monoterpene (optionally terpineol, myrcene, limonene, linanool, or pinene); a sesquiterpene (optionally humulene, famesenes, or farnesol); a diterpene (optionally retinol, retinal, or phytol); a sesterterpene (optionally geranylfamesol); a triterpene (optionally squalene, lanosterol or cycloartenol); a sesquarterpene (optionally ferrugicadiol or tetraprenylcurcumene) or a tetraterpene (optionally lycopene), or any combination thereof; or, the terpene solvent comprises a terpene alcohol or a terpenoid; or, the terpene solvent or terpenoid alcohol solvent comprises: geraniol, perillyl alcohol or terpineol, optionally alpha-terpineol; or, the terpenoid solvent comprises: a hemiterpenoid, a monoterpenoid, a sesquiterpenoid, a diterpenoid or a ginkgolide, a sesterterpenoid, a triterpenoid or a sterol, a tetraterpenoid or a carotenoid, a polyterpenoid or any combination thereof;
- the extracted terpene comprises: humulene, pinene (optionally α-pinene), myrcene, limonene, linanool, caryophylene, carene, camphene, dipentene, terpinolene or turpentine, or any combination thereof; or, the extracted terpene comprises: a hemiterpene (optionally a prenol or an isovaleric acid); a monoterpene (optionally terpineol, myrcene, limonene, linanool, or pinene); a sesquiterpene (optionally humulene, farnesenes, or farnesol); a diterpene (optionally retinol, retinal, or phytol); a sesterterpene (optionally geranylfarnesol); a triterpene (optionally squalene, lanosterol or cycloartenol); a sesquarterpene (optionally ferrugicadiol or tetraprenylcurcumene) or a tetraterpene (optionally lycopene), or any combination thereof; or, the extracted terpene comprises a terpene alcohol or a terpenoid; or, the extracted terpenoid alcohol comprises: geraniol, perillyl alcohol or terpineol, optionally alpha-terpineol; or, the extracted terpenoid comprises: a hemiterpenoid, a monoterpenoid, a sesquiterpenoid, a diterpenoid or a ginkgolide, a sesterterpenoid, a triterpenoid or a sterol, a tetraterpenoid or a carotenoid, a polyterpenoid or any combination thereof;
- the extracted cannabinoid comprises a $\Delta^9$tetrahydrocannabinol ($\Delta^9$ THC); cannabidiol (CBD); cannabinol (CBN); cannabigerol (CBG); cannabichromene (CBC); cannabidivarol (CBDV); tetrahydrocannabidiol (THCBD); tetrahydrocannabigerol (THCBG); tetrahydrocannabichromene (THCBC); tetrahydrocannabidivarol (THCBDV), $\Delta^9$-tetrahydrocannabivarin ($\Delta^9$-THCV) or combinations thereof;
- the hemp or *cannabis* plant or plant part, other than harvesting or collecting, is unprocessed or has not been physically processed, or has not been exposed to: a solvent or aqueous solution; a heating or drying process; a dehydration process; a crushing process; and/or, a chopping, macerating or mincing process, since its harvest;
- the hemp or *cannabis* plant or plant part, other than harvesting or collecting, is subjected to: a heating or drying process; a dehydration process; a crushing process; and/or, a chopping, macerating or mincing process, since its harvest;
- the plant of the family Cannabaceae is a plant of the genus *Cannabis, Humulus* or *Celtis*, and optionally the plant of the genus *Cannabis* is a *Cannabis* saliva, *Cannabis indica* or a *Cannabis ruderalis*;
- a trichome or trichome fraction is isolated, or is substantially isolated, from the hemp or *cannabis* plant or plant part, and it is the isolated or substantially isolated trichome or trichome fraction that is contacted with the solvent; and/or the industrial process or method comprises continuously extracting the cannabinoid or the terpene from the hemp or *cannabis* plant or plant part, by a method comprising:

(a) feeding the hemp or *cannabis* plant or plant part into a vessel;

(b) feeding the solvent into the vessel to: saturate or substantially saturate the hemp or *cannabis* plant or plant part in the vessel with the solvent to create a mixture of solvent and hemp or *cannabis* plant or plant part, thereby dissolving the cannabinoid or the terpene in or into the solvent, wherein optionally the vessel is heated before and/or during the feeding and/or saturating process, and optionally the vessel is heated to or kept warm or hot to: between about 30° C. and 300° C., or to between about 35° C. and 200° C., or between about 37° C. and 100° C., and optionally the vessel is cooled and/or kept cool before and/or during the feeding and/or saturating process, and optionally the vessel is cooled or kept cool to between about −20° C. and 37° C., or is cooled or kept cool to between about −18° C. and 22° C., or is cooled or kept cool to between about −10° C. and 0° C., and optionally the mixture is agitated during all or part of the saturating process, and optionally the solvent is removed, or substantially removed, from the vessel, and optionally only the solvent is removed, or substantially removed, from the vessel, or substantially most of the cannabinoid or the terpene remains in the vessel after removal of the solvent.

In alternative embodiments of the industrial processes or methods as provided herein:

the solvent further comprises: an aliphatic hydrocarbon, a 1,4 dioxane, a chloroform, a dichloromethane, a diethyl ether, acetone, benzene or a substituted benzene, toluene, a xylene, ethyl acetate, propyl acetate, butyl acetate, tetrahydrofuran, tetrahydropyran, acetone, benzene or a substituted benzene, toluene, a xylene, ethyl acetate, propyl acetate, butyl acetate, tetrahydrofuran, tetrahydropyran, or an alcohol or any mixture thereof, and optionally the aliphatic hydrocarbon comprises a pentane, a cyclopentane, a hexane, a cyclohexane, a heptane, diethyl ether, dipropyl ether, dibutyl ether or any mixture thereof;

the solvent comprises at least one organic alcohol, and optionally the at least one organic alcohol comprises methanol, ethanol, propanol, isopropanol, butanol, pentanol, hexanol, heptanol or octanol or a mixture thereof;

the treating or exposing of the hemp or *cannabis* to the solvent lasts for a period of between about 1 minute to about 48 hours, or for a period of time of between about 1 minute to 60 minutes, between about 1 minute to 120 minutes, or between about 1 minute to 480 minutes;

the treating or exposing of the hemp or *cannabis* to the solvent comprises immersion, spraying, washing, counter current liquid solid contacting or any combination thereof;

the solvent fraction of the extraction solvent is substantially removed after the extraction solvent comprising an extracted hemp or *cannabis* comprising the cannabinoid or the terpene from the hemp or the *cannabis* plant or plant part is produced;

the solvent is substantially removed by a process comprising using a screw press (optionally a dewatering screw press) or a sludge press, spray drying, air stripping, gas stripping, vacuum stripping, heating, evaporation, washing or any combination thereof;

before the treating or exposing of the hemp or *cannabis* to the solvent the hemp or *cannabis* is fed through a conveyor into an extraction unit, and optionally is sprayed or continuously sprayed with the solvent;

the hemp or the *cannabis* plant or plant part is not dried before the treating or exposing of the hemp or *cannabis* to the solvent; or, the hemp or the *cannabis* plant or plant part is substantially wet, optionally comprising greater than about 50%, 60%, 70%, or 80% or more moisture, or is between about 40% and 90% moisture (or optionally the hemp or the *cannabis* plant or plant part is about 50%, 60%, 70%, 80% or 90% or more water by weight), before the treating or exposing of the hemp or *cannabis* to the solvent.

The details of one or more exemplary embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

DESCRIPTION OF DRAWINGS

Like reference symbols in the various drawings indicate like elements.

DETAILED DESCRIPTION

Figure 1:
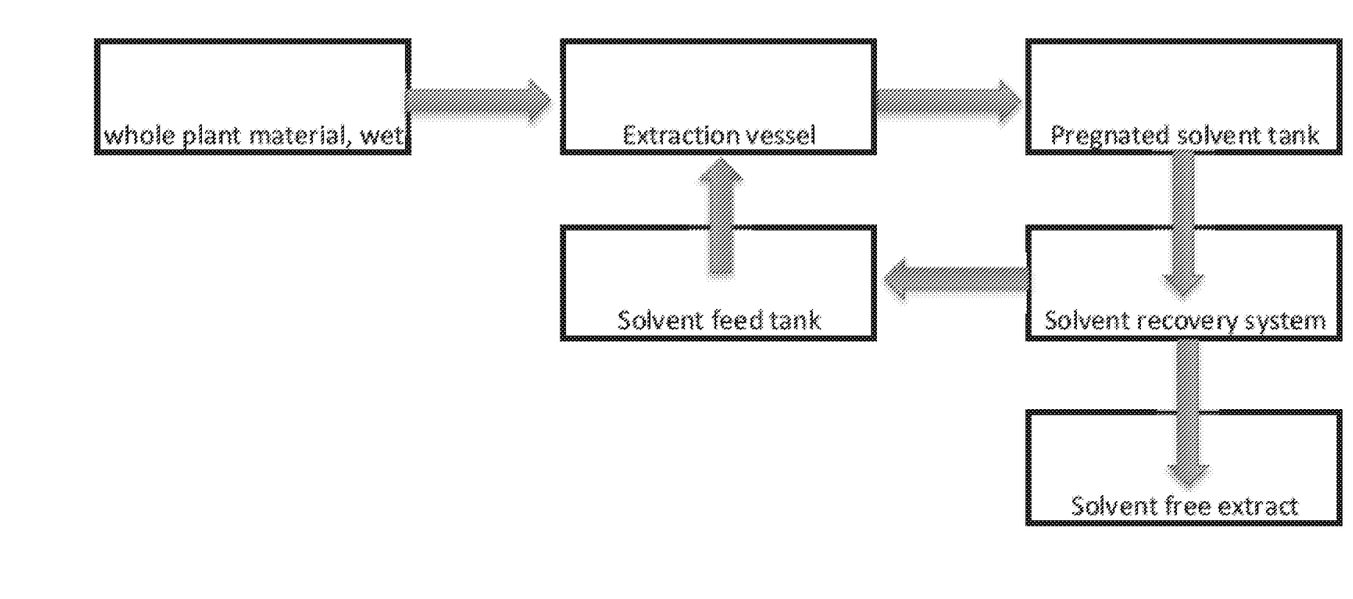
FIG. 1 illustrates an exemplary process as provided herein to extract and separate products *cannabis* species.

In alternative embodiments, provided are industrial processes and methods for extracting or removing cannabinoids and terpenes from plant trichomes. In alternative embodiments, the cannabinoids and terpenes are extracted or removed from the plant trichomes using a non-polar or an organic solvent.

A key aspect of the industrial processes and methods as provided herein is understanding the nature and location of the target cannabinoids and terpenes when extracting from a plant trichome, e.g., from a hemp or a *Cannabis*. The cannabinoids, and many terpenes, are primarily located in the trichomes, which exist on the surface of the plant, primarily on the flower. The actual definition of trichome is "fine outgrowths or appendages on plants, algae, lichens, and certain protists." Originating from the Greek word "Trichōma," meaning "growth of hair," these tiny microscopic mushroom-looking protuberances are the very factories that produce the hundreds of known cannabinoids, terpenes, and flavonoids.

Cannabinoid synthesis within the trichome begins as *cannabis* plants move into their bloom phase. As they begin to produce flowers, trichomes form along the outer surface of the above-ground plant vegetation and begin to transport vacuoles and plastids from their stalk into the gland head. At this point, cells within the gland head will begin to metabolize and form precursors for what will eventually become cannabinoids. The rate and concentration at which a *cannabis* plant produces trichomes will be contingent on both genetics well as some environmental factors. Though plants containing higher concentrations of trichomes don't always produce the highest concentration of cannabinoids and/or terpenes, variables such as UV light greatly affect cannabinoid and terpene synthesis within the trichome head.

Whether alive on a vine or harvested, trichomes are incredibly volatile and risk destruction and/or degradation at the hands of many catalysts, including but not limited to: physical contact or agitation, heat, light, oxygen and time. Not only do the trichomes themselves risk damage when exposed to these elements, but the essential oils within them risk degradation. There are ways to dramatically slow degradation of trichomes by carefully handling *cannabis* flowers both during propagation and post-harvest. By limiting physical contact and agitation to the flowers themselves, trichomes may be preserved on the plant for longer periods of time. Those looking to extend the shelf life of trichomes beyond that of the plants they came from often resort to extraction techniques. An extraction in this context may be defined as the process of either mechanically or chemically removing trichomes from the plant itself.

With the location of the cannabinoids and terpenes determined we now need to understand the nature of the cannabinoids and terpenes present in the trichomes. Cannabinoids and cannabinoid acid species can be broadly understood as being non-polar. Terpenes and flavonoids present in the trichome as well can be broadly understood as non-polar. An aspect of the current industrial practice of hand separating the flowers from the stems causes physical damage to the trichomes and likely trichome losses. In addition, the drying process causes additional losses of volatile terpenes to the atmosphere. Therefore, methods as provided herein for extracting cannabinoids, terpenes and flavonoids from a whole wet plant will minimize the physical handling losses, and eliminating the drying process will help preserve valuable terpenes and eliminate the energy required for drying of the plant material.

In alternative embodiments, an organic non-polar solvent is used to wash and dissolve cannabinoids and terpenes from e.g., a whole wet plant, trichome or trichome fraction, or the pubescent plant, algae or lichen. The use of an organic non-polar solvent to wash and dissolve the cannabinoids and terpenes present in the trichomes can be a straightforward protocol when water is present. The organic non-polar solvent saturated with cannabinoids and terpenes will phase separate from any water that may or may not be present in the extract solution after contacting.

In alternative embodiments, a polar organic solvent, e.g., a polar organic solvent immiscible in water is used to wash and dissolve cannabinoids and terpenes from e.g., a whole wet plant, trichome or trichome fraction, or the pubescent plant, algae or lichen. In some embodiments, use of polar, organic solvents that is immiscible in water such as pentanol, hexanol or octanol also can be a straightforward protocol when water is present—the polar, organic solvents immiscible in water (e.g., pentanol, hexanol or octanol) phase separates from water.

In alternative embodiments, provided herein are batch, semi-continuous batch or continuous processes which offer significant improvements and advantages over current techniques used. In alternative embodiments, whole plants are mechanically harvested using e.g., a combine and sickle bar or a similar whole plant cutting device, and then taken for extraction, thereby eliminating the manual labor associated with hand harvesting and the energy needed for drying.

In alternative embodiments, non-polar solvent used in processes and methods as provided herein comprise: aliphatic hydrocarbons, pentane, cyclopentane, hexane, cyclohexane, heptane, cyclohentane, a pentene, a cylcopentene, a hexene, a cylohexene, acetone, a benzene or a substituted benzene, toluene, a xylene (e.g., o-xylenes, m-xylene, p-xylene), methyl acetate, ethyl acetate, propyl acetate, butyl acetate, tetrahydrofuran, tetrahydropyran, diethyl ether, dipropyl ether, dibutyl ether, 1,4-dioxane, chloroform, dichloromethane, dichloroethane, freon, a terpene, a hemiterpene, a monoterpene, a diterpene, limonene, humulene, pinene, myrcene, limonene, linanool, or caryophylene or any combination or mixture thereof.

In alternative embodiments, the trichome or trichome fraction, or the pubescent plant, algae or lichen, biomass used in extraction can comprise wet material, dried material, stock stems and leaves can be removed or present. Wet material can be present in combination with dried material at any ratio. The biomass can be sized reduced or a whole plant.

In alternative embodiments, the trichome or trichome fraction, or the pubescent plant, algae or lichen, biomass (e.g., the hemp or *Cannabis* biomass) is processed with the at least one solvent, e.g., non-polar, organic solvent; polar, organic solvent, or mixture thereof. Techniques for processing comprise immersion, spraying, washing, intermittent immersion, continuous counter current or co-current liquid solid contacting. Solvent biomass contacting can range for a period of 1 minute to 48 hours.

In one embodiment, hemp or *Cannabis* is used as the material to process. There are different ways to prepare the hemp or *Cannabis* for extraction. Typically flower of the female plant contain the highest quantities of cannabinoids. The preparation can comprise whole intact wet plant, whole intact dry plant material, chopped whole wet plant, chopped whole dry plant, wet flower and leaf, dry flower and leaf, or any combination thereof.

In alternative embodiments, the plant material comprises flowering plants in the family Cannabaceae. *Cannabis sativa, Cannabis indica, Cannabis ruderalis*, hemp or any combination thereof.

In alternative embodiments, the plant material is fed into a vessel using a surge bin, a metered hopper, or an auger or other device. If the device is to be used in a continuous fashion, the feed system will be configured to provide a constant volume of the prepared feedstock. In that regard, the feed method will require a reservoir of some type or in itself be a continuously fed device.

In alternative embodiments, the plant material, e.g., the pubescent plant, algae or lichen, is contacted with the at least one solvent, e.g., non-polar, organic solvent; polar, organic solvent, or mixture thereof. In alternative embodiments, the methods comprise immersion, spraying, washing, counter current liquid solid contacting or any combination thereof.

In alternative embodiments, the non-polar, organic solvent comprises at least one of: aliphatic hydrocarbons, pentane, cyclopentane, hexane, cyclohexane, heptane, acetone, benzene, toluene, xylenes, ethyl acetate, propyl acetate, butyl acetate, tetrahydrofuran, tetrahydropyran, diethyl ether, dipropyl ether, dibutyl ether, 1,4-dioxane, chloroform, dichloromethane, a terpene, a terpenoid, a hemiterpene, a monoterpene, a diterpene, limonene, humulene, pinene, myrcene, caryophylene, limonene, linanool, or any combination thereof.

In alternative embodiments, the cannabinoids and terpenes are dissolved from the surface of the plant material by the one or more solvents (e.g., at least one non-polar, organic solvent; polar, organic solvent; or, mixture thereof) contacting the surface of the plant material. The extracted biomass is then processed for residual solvent, e.g., residual solvent is removed or substantially removed. Techniques known to those skilled in the art (e.g., for the contacting of the solvent with the plant material) comprise using a screw press (optionally a dewatering screw press) or a sludge press, spray drying, air stripping, gas stripping, vacuum stripping, heating, evaporation, washing or any combination thereof.

In alternative embodiments, the cannabinoid, flavonoid and/or terpene rich solvent solution is then processed to separate the solvent from the cannabinoids and/or terpenes, or, in the case of winterization or crystallization, to separate the cannabinoids and/or terpenes from the solvent. Techniques that can be used for this separation can include any known to those skilled in the art, including batch distillation, continuous distillation, vacuum distillation, gas stripping, mole sieve filtration, nano filtration, filtration, winterization or crystallization, or any combination thereof. In alternative embodiments, the processed or recovered solvent or solvent mixture is then recycled, stored for future use and/or disposed.

In alternative embodiments, a whole wet trichome or trichome fraction, or the pubescent plant, algae or lichen (collectively and individually referred to a "biomass"), e.g., hemp is fed through a conveyor into an extraction unit. The biomass, e.g., hemp, can be continuously sprayed with: the at least one non-polar, organic solvent, e.g., a terpene or terpene mixture or any combination thereof; or, a mixture of at least one polar, organic solvent and at least one non-polar and organic solvent; or, at least one polar, organic solvent, e.g., an organic alcohol.

In alternative embodiments, the biomass, e.g., hemp, is contacted with the solvent for a period of time from 1 minute to 60 minutes, 1 minute to 120 minutes, 1 minute to 480 minutes. In alternative embodiments, the solvent drains through the biomass and is collected. In alternative embodiments, the collected solvent or solvent mixture is reintroduced, e.g., as the biomass continuously travels on a conveyor through a solvent contacting system. In alternative embodiments, the biomass, e.g., hemp, is contacted with the solvent or solvent mixture at the temperature ranging from between about −10° C. to the boiling point of the solvent used, or from between about −10 to 100° C. for a period of time from between 1 second to 480 minutes, or between about 1 minute (min) and 1 hour (hr), or between about 5 min and 2 hours, with or without agitation during all or part of the process.

In alternative embodiments, the biomass is introduced to a mixing tank, with or without heating. In alternative embodiments, the biomass is introduced into the mixing tank at a temperature of between about −10 to 100° C., or between about −5 to 80° C., or the temperature of the biomass is in the mixing tank raised to or lowered to, or kept at, at a temperature of between about −10 to 100° C., or between about −5 to 80° C.

In alternative embodiments, the solvent or solvent mixture is introduced to the tank in sufficient quantity as to provide for complete or near complete immersion of the biomass. In alternative embodiments, the biomass and solvent or solvent mixture are then subjected to mixing; however, mixing is not necessary but can improve extract yield. In alternative embodiments, the biomass is then removed or filtered from the solvent or solvent mixture.

In alternative embodiments, the solvent or solvent mixture is then removed by evaporation and optionally the cannabinoids and/or terpenes are recovered. In alternative embodiments, the solvent or solvent mixture is then removed by a rotary evaporator or other evaporating equipment, optionally at the temperature below the boiling point of the solvent or solvent mixture under a pressure ranging from between about the atmosphere pressure down to about 0.001 torr.

Winterization or Crystallization

In alternative embodiments, the cannabinoids and/or terpenes are recovered from (or substantially recovered from), or isolated from the solvent or solvent mixture by a winterization or crystallization process.

In alternative embodiments, before winterization or crystallization (or solidification) the initial cannabinoids and/or terpenes solvent mixture is (further) diluted with an organic solvent, e.g., a hexane or a terpene. In alternative embodiments, before winterization or crystallization the solvent mixture is diluted by between about 1% to 80%, or by between about 5% to 50%.

In alternative embodiments, before winterization or crystallization (or solidification) the initial cannabinoids and/or terpenes solvent mixture is concentrated, e.g., a portion of the non-polar, organic solvent or polar, organic solvent is removed before the winterization or crystallization (or solidification), or cooling, process.

In alternative embodiments, between about 1% to 90% of the non-polar, organic solvent or polar, organic solvent is removed before the winterization or crystallization (or solidification), or cooling, process.

In alternative embodiments, the winterization or crystallization (or solidification), or cooling, process comprises cooling the mixture until crystals of cannabinoids, flavonoids and terpenes are formed, or until the cannabinoids, flavonoids and/or terpenes solidify. In alternative embodiments, the cooling process comprise further cooling after the crystallization (or solidification) begins. In alternative embodiments, the winterization or crystallization (or solidification), or cooling, process comprises cooling the mixture to a temperature of between about −10° C. to about −90° C., between about −20° C. to about −85° C., or between about −50° C. to about −80° C. In alternative embodiments, the winterization or crystallization (or solidification), or cooling, process comprises cooling for between about 10 to 30 minutes (min) to about 1, 2, 3, 4, 5 or 6 hours (hrs). In alternative embodiments, the winterization or crystallization (or solidification), or cooling, process lasts for between about 1 to 24 hrs. In alternative embodiments, the process comprises multiple cooling, crystal harvesting or isolation, and re-cooling cycles.

In alternative embodiments, the winterization or crystallization (or solidification), or cooling, process comprises a process as described in U.S. Pat App Pub no US2017/0008870A1; U.S. Pat. No. 3,755,389; or U.S. Pat. No. 2,705,723.

In alternative embodiments, the winterization or crystallization (or solidification), or cooling, process is done in a refrigerator, a freezer or using dry ice (or any system that lowers the temperature to about −109.3 degrees Fahrenheit (−78.5 degrees C.)) or liquid nitrogen. The winterization or crystallization (or solidification), or cooling, process can be done under vacuum or pressure.

In alternative embodiments, the solids or crystals of the cannabinoids, flavonoids and/or terpenes are separated from the liquid solvent by filtration. In alternative embodiments, the solids or crystals of the cannabinoids, flavonoids and/or terpenes are decanted away from the liquid solvent. In alternative embodiments, the solids or crystals of the cannabinoids, flavonoids and/or terpenes are sheet or ball crystals. In alternative embodiments, the solids or crystals of the cannabinoids, flavonoids and/or terpenes need to be scraped or physically removed from the container or reaction vessel from which they were cooled and subsequently crystallized or solidified.

In alternative embodiments, the cannabinoid, flavonoid and/or terpene solids or crystals are at least 70% pure, or are between about 75% to 99.9% or 100% pure (e.g., free of impurities, or non-cannabinoid, flavonoid and/or terpene substances or solvent), or are about (or at least about) 75%, 80%, 85%, 90%, 95%, 98%, 99%, 99.5%, 99.9% or 100% pure.

It is understood that those skilled in the art might find alternative embodiments to the methods described herein, which are meant to describe the principles involved in the extraction conditions, which include the collection of the extractants and solvent, the collection of the extractants or solutes (the compounds of interest being isolated), and/or the removal of the spent material, the subsequent separation of the extractant from the solvent, and the optional step or steps of isolating one or more of the products of the extraction, where these alternative embodiments fall within the scope of this methods as provided herein.

Any of the above aspects and embodiments can be combined with any other aspect or embodiment as disclosed here in the Summary and/or Detailed Description sections.

As used in this specification and the claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

The invention will be further described with reference to the examples described herein; however, it is to be understood that the invention is not limited to such examples.

EXAMPLES

Example 1: Exemplary Methods 10 pounds of mature whole hemp plant was harvested. Between about 3 gram (g) to about 100 g samples of plant flower, leaf and stem was weighed for the experiments. The material was not dried or subjected to particle size reduction.

Three (3) samples of whole wet plant material was then prepared for extraction. Sample 257-A (control sample) was immersed in 1,500 ml of 65:35 mixture of chloroform:methanol overnight; sample 257-B was subjected to 5×60 second immersions in ambient hexane; sample 257-C was immersed in hexane for 15 minutes at ambient temperature; sample 257-D was immersed in hexane for 15 minutes at 40 C; sample 257-E was immersed in hexane for 10 minutes at 60 C.

100 g of the weighed sample was immersed in dichloromethane (DCM) in a vessel at ambient temperature, and then the sample was taken out. This immersion was repeated 5 times. Another three 100 g samples were soaked in hexane in three different vessels with agitation under the conditions: at ambient temperature for 15 min; at 40° C. for 15 min; 60° C. for 15 min. A control sample was subjected to a 1,500 ml 65:35 mixture chloroform:methanol solution and let soak for 24 hours with agitation to represent 100% extraction of cannabinoids and used as a reference of total extractable cannabinoids.

| Exp No. | Extraction Method (100 g wet hemp in 1500 mL solvent) | Weight of dried extract (g) | Percentage of CBD in dried oil (%) | CBD weight in dried oil (g) | CBD weight extracted from 100 g wet hemp (g) | Percentage of CBD in 100 g wet hemp |
|---|---|---|---|---|---|---|
| 257-A | immersion in chloroform/methanol at ambient temperature overnight | 5.3119 | 34.7 | 1.84 | 1.84 | 1.84 |
| 257-B | 5 × 60 sec immersion in dichloromethane | 2.2821 | 62.6 | 1.43 | 1.43 | 1.43 |

-continued

| Exp No. | Extraction Method (100 g wet hemp in 1500 mL solvent) | Weight of dried extract (g) | Percentage of CBD in dried oil (%) | CBD weight in dried oil (g) | CBD weight extracted from 100 g wet hemp (g) | Percentage of CBD in 100 g wet hemp |
|---|---|---|---|---|---|---|
| 257-C | immersion in ambient temperature hexane for 15 min | 2.7476 | 64.7 | 1.78 | 1.78 | 1.78 |
| 257-D | immersion in 40° C. hexane for 15 min | 3.3073 | 66.2 | 2.19 | 2.19 | 2.19 |
| 257-E | immersion in 60° C. hexane for 10 min | 2.2014 | 65.0 | 1.43 | 1.43 | 1.43 |

A number of embodiments of the invention have been described. Nevertheless, it can be understood that various modifications may be made without departing from the spirit and scope of the invention. Accordingly, other embodiments are within the scope of the following claims.

We claim:

1. A method of producing a winterized, isolated cannabidiol the method comprising the steps of:
   a) isolating a trichome from *cannabis*;
   b) extracting the trichome of the *cannabis* using a first solvent selected from the group consisting of limonene, myrcene, pinene, humulene, geraniol, perillyl alcohol, terpineol, and mixtures thereof to produce a first extract of the trichome of the *cannabis* consisting essentially of cannabidiol;
   wherein the limonene, myrcene, pinene, humulene, geraniol, perillyl alcohol and terpineol used for extraction are not derived from the trichome of the *cannabis*;
   c) distilling the first extract of the trichome of the *cannabis* in (b) consisting essentially of the cannabidiol to produce a first isolate the cannabidiol;
   d) extracting the first isolate of the cannabidiol using a second solvent selected from the group consisting of 1,4 dioxane, chloroform, dichloromethane, diethyl ether, acetone, benzene, toluene, xylene, ethyl acetate, propyl acetate, butyl acetate, tetrahydrofuran, tetrahydropyran, hexane, pentane, heptane, and mixtures thereof to produce a second isolate of the cannabidiol; and
   e) winterizing the distilled, second isolate of the cannabidiol of (d) to produce a winterized, isolated cannabidiol.

2. The method of claim 1, wherein the trichome of *cannabis* is from *Cannabis sativa*, *Cannabis* indica or *Cannabis ruderalis*.

3. The method of claim 1, wherein the pinene is α-pinene.

4. The method of claim 1, wherein the trichome of *cannabis*, other than harvesting or collecting, is unprocessed or has not been physically processed, or has not been exposed to a solvent solution, an aqueous solution, a heating process, a drying process, a dehydration process, a crushing process, a chopping process, a macerating process or a mincing process, since its harvest.

5. The method of claim 1, wherein the trichome of *cannabis* is subjected to a heating process, a drying process, a dehydration process, a crushing process, a chopping process, a macerating process or a mincing process, since its harvest.

6. The method of claim 1, wherein the extracting of the cannabinol from the isolated trichome from *cannabis* using the first solvent consists essentially of: (a) feeding the trichome of *cannabis* into a vessel; and (b) feeding the first solvent into the vessel to saturate or substantially saturate the trichome of *cannabis* in the vessel with the first solvent to create a mixture of the first solvent and the trichome of *cannabis*, thereby dissolving the trichome of *cannabis* into the first solvent.

7. The method of claim 6, wherein the vessel is heated before and/or during the feeding and/or saturating or dissolving process for between about 5 min and 5 hrs.

8. The method of claim 6, wherein the vessel is heated to or kept warm or hot between about 30° C. and 300° C.

9. The method of claim 8, wherein the vessel is heated to or kept warm or hot between about 35° C. and 200° C.

10. The method of claim 9, wherein the vessel is heated to or kept warm or hot between about 37° C. and 100° C.

11. The method of claim 1, wherein the vessel is cooled and/or kept cool before and/or during the feeding and/or saturating or dissolving process.

12. The method of claim 6, wherein the vessel is cooled or kept cool before and/or during the feeding and/or saturating or dissolving process, and the contact time is between about 1 hr and 48 hrs.

13. The method of claim 7, wherein the vessel is cooled or kept cool before and/or during the feeding and/or saturating or dissolving process, and the contact time is between about 2 hrs and 36 hrs.

14. The method of claim 8, wherein the vessel is cooled or kept cool before and/or during the feeding and/or saturating or dissolving process, and the contact time is between about 3 hrs and 24 hrs.

15. The method of claim 9, wherein the vessel is cooled or kept cool to between about −20° C. and 37° C.

16. The method of claim 10, wherein the vessel is cooled to between about −18° C. and 22° C.

17. The method of claim 6, wherein the mixture is agitated during all or part of the saturating process.

18. The method of claim 1, wherein the treating or exposing of the trichome of *cannabis* to the first solvent lasts for a period of between about 1 minute to about 48 hours.

19. The method of claim 18, wherein the treating or exposing of the trichome of *cannabis* to the first solvent lasts for a period of between about 1 minute to 60 minutes.

20. The method of claim 1, wherein the treating or exposing of the trichome of *cannabis* to the first solvent is immersion, spraying, washing, counter current liquid solid contacting or any combination thereof.

21. The method of claim 1, wherein before the treating or exposing of the trichome of *cannabis* to the first solvent the *cannabis* is fed through a conveyor into an extraction unit and is sprayed or continuously sprayed with the first solvent.

22. The method of claim 1, wherein the trichome of *cannabis* is not dried before the treating or exposing of the *cannabis* to the first solvent.

23. The method of claim 1, wherein the trichome *cannabis* is substantially wet before the treating or exposing of the *cannabis* to the first solvent.

24. The method of claim 1, wherein the distillation is batch distillation, continuous distillation or vacuum distillation.

* * * * *